US011392872B2

(12) United States Patent
Compton et al.

(10) Patent No.: US 11,392,872 B2
(45) Date of Patent: Jul. 19, 2022

(54) OPTIMIZING WORKFLOWS

(71) Applicant: CERNER INNOVATIONS, INC., Kansas City, KS (US)

(72) Inventors: David Compton, Lenexa, KS (US); James D. Eaton, Jr., Gardner, KS (US); Matthew Gadzinski, Mission, KS (US); Brannon Garvert, Kansas City, MO (US); Mario Manese, Kansas City, MO (US); Justin Nelson, Merriam, KS (US); David Pierre, Leawood, KS (US)

(73) Assignee: CERNER INNOVATION, INC., North Kansas City, KS (US)

( * ) Notice: Subject to any disclaimer, the term of this patent is extended or adjusted under 35 U.S.C. 154(b) by 964 days.

(21) Appl. No.: 14/585,306

(22) Filed: Dec. 30, 2014

(65) Prior Publication Data

US 2015/0120327 A1    Apr. 30, 2015

Related U.S. Application Data

(63) Continuation of application No. 12/981,784, filed on Dec. 30, 2010, now Pat. No. 10,460,266.

(51) Int. Cl.

| G06Q 10/06 | (2012.01) |
| G16H 10/60 | (2018.01) |
| G16H 40/20 | (2018.01) |
| G16B 40/20 | (2019.01) |
| G06Q 30/00 | (2012.01) |

(52) U.S. Cl.
CPC . *G06Q 10/0633* (2013.01); *G06Q 10/063112* (2013.01); *G06Q 30/018* (2013.01); *G16B 40/20* (2019.02); *G16H 10/60* (2018.01); *G16H 40/20* (2018.01)

(58) Field of Classification Search
CPC .... G06Q 50/22; G06Q 50/24; G06Q 10/0633; G06Q 10/063112; G06Q 30/018; G16H 40/20; G16H 10/60
See application file for complete search history.

(56) References Cited

U.S. PATENT DOCUMENTS

| 6,456,239 B1 | 9/2002 | Werb et al. |
| 6,804,656 B1 | 10/2004 | Rosenfeld et al. |
| 7,333,002 B2 | 2/2008 | Bixler et al. |

(Continued)

OTHER PUBLICATIONS

Preinterview First Office Action Communication dated May 22, 2012 in U.S. Appl. No. 121981,784, 5 pages.

(Continued)

*Primary Examiner* — Eliza A Lam
(74) *Attorney, Agent, or Firm* — Shook Hardy & Bacon, L.L.P.

(57) ABSTRACT

Methods, systems, and computer storage media are provided for optimizing workflows by monitoring a healthcare environment. Data may be compiled from various sources to monitor interactions within the healthcare environment. Both interactions with individuals and interactions with a healthcare system may be monitored. Each of location data, clinical data, and system data, among others, may be combined to monitor the healthcare environment. By combining the data from various sources, a user is able to get a complete picture of the healthcare environment.

19 Claims, 5 Drawing Sheets

(56) References Cited

U.S. PATENT DOCUMENTS

| | | | |
|---|---|---|---|
| 7,890,349 | B2 | 2/2011 | Cole et al. |
| 7,895,055 | B2 | 2/2011 | Schneider et al. |
| 7,908,153 | B2 | 3/2011 | Scherpbier et al. |
| 7,945,457 | B2 | 5/2011 | Zaleski |
| 7,962,544 | B2 | 6/2011 | Torok et al. |
| 8,121,859 | B2 | 2/2012 | Becker et al. |
| 8,332,240 | B1 | 12/2012 | Garver et al. |
| 8,346,572 | B2 | 1/2013 | Eaton, Jr. et al. |
| 8,565,500 | B2 | 10/2013 | Neff |
| 8,583,451 | B2 | 11/2013 | Anuszewski et al. |
| 8,769,153 | B2 | 7/2014 | Dziubinski |
| 2003/0229514 | A2 | 4/2003 | Brown |
| 2005/0021369 | A1 | 1/2005 | Cohen et al. |
| 2005/0149358 | A1* | 7/2005 | Sacco et al. ............ 705/2 |
| 2007/0129983 | A1 | 6/2007 | Scherpbier et al. |
| 2008/0001763 | A1* | 1/2008 | Raja et al. ............ 340/573.1 |
| 2008/0164998 | A1* | 7/2008 | Scherpbier et al. ..... 340/539.13 |
| 2009/0206992 | A1 | 8/2009 | Giobbi et al. |
| 2010/0169121 | A1 | 7/2010 | Herbst et al. |
| 2012/0095779 | A1 | 4/2012 | Wengrovitz et al. |
| 2013/0110535 | A1 | 5/2013 | Eaton et al. |
| 2014/0365242 | A1 | 12/2014 | Neff |
| 2016/0070869 | A1 | 3/2016 | Portnoy |

OTHER PUBLICATIONS

Notice of Allowance dated May 27, 2014 in U.S. Appl. No. 12/981,784, 10 pages.

Pending U.S. Appl. No. 14/584,689, filed Dec. 29, 2014, titled "System Assisted Data Blending", first Inventor Alan Harris Staples II.

Non-Final Office Action dated Aug. 21, 2017 in U.S. Appl. No. 14/671,916, 18 pages.

First Action Interview Office Action dated Aug. 9, 2012 in U.S. Appl. No. 12/981,784, 6 pages.

Final Office Action dated Jan. 30, 2014 in US. Appl. No. 12/981,784, 8 pages.

Non-Final Office Action dated Oct. 9, 2014 in U.S. Appl. No. 12/981,784, 4 pages.

Final Office Action dated Mar. 19, 2015 in U.S. Appl. No. 12/981,784, 8 pages.

Non-Final Office Action dated Apr. 4, 2018 in U.S. Appl. No. 12/981,784, 6 pages.

* cited by examiner

OPTIMIZING WORKFLOWS

CROSS REFERENCE TO RELATED APPLICATIONS

This application is a continuation of and claims priority from U.S. patent application Ser. No. 12/981,784 (now U.S. Pat. No. 10,460,266), filed Dec. 30, 2010, and entitled "Optimizing Workflows," the entire contents of which is herein incorporated by reference.

BACKGROUND

Healthcare spending is at an all time high. Healthcare environments are constantly seeking solutions that support improvements that impact their bottom line. Return on investment (ROI) is critical in making decisions regarding, for example, software solutions, process changes, other advanced technologies, or the like.

Current methodologies for determining benefits, either quantitative or qualitative, from various changes are most often subjective in nature. This is primarily due to a lack of concrete information about how an introduced change has impacted or will impact an environment in either a positive or negative way.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to optimizing workflows by compiling data from various sources to monitor interactions within a healthcare environment. Both interactions with individuals and interactions with a healthcare system may be monitored. Location data, clinical data, and system data, among others, may be combined to monitor the healthcare environment. By combining the data from various sources, a user is able to get a complete picture of the healthcare environment to, for example, optimize workflows.

Accordingly, in one aspect, the present invention is directed to one or more computer storage media storing computer-useable instructions that, when used by one or more computing devices, cause the one or more computing devices to perform a method. The method includes receiving a location of a clinician, clinical information, and one or more user selections representing a clinical event. Based on the clinical event, the clinical information, and the location of the clinician, a timeline is generated including the clinical event.

In another aspect, the present invention is directed to a computerized system for compiling clinical information. The system includes a locating component for locating clinicians, a first receiving component for receiving location information from the locating component, a second receiving component for receiving clinical information from a clinical database, a third receiving component for receiving one or more user selections, an identifying component for identifying a clinical event represented by the one or more user selections, and a generating component for generating a view of a healthcare environment based on the clinical event, the clinical information, and the location information.

In yet another aspect, the present invention is directed to one or more computer storage media storing computer-useable instructions that, when used by one or more computing devices, cause the one or more computing devices to perform a method. The method includes receiving a location of a clinician, clinical information, and one or more user selections representing a clinical event. Based on the clinical event, the clinical information, and the location of the clinician, one or more suggestions to modify a workflow represented in a view of the healthcare environment are communicated.

BRIEF DESCRIPTION OF THE DRAWINGS

The present invention is described in detail below with reference to the attached drawing figures, wherein.

DETAILED DESCRIPTION

Figure 1:
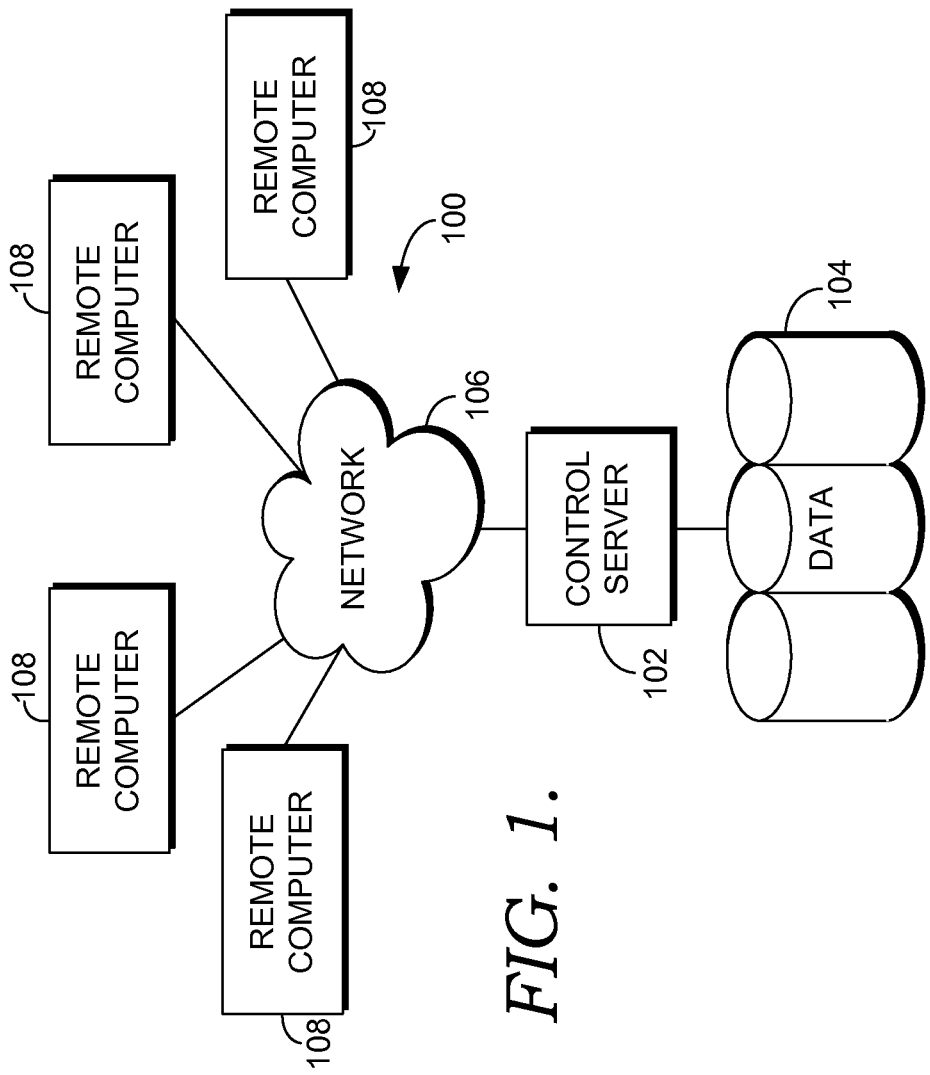
FIG. 1 is a block diagram of an exemplary computing environment suitable for use in implementing the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention provide for systems, methods, and computer storage media for optimizing workflows. Data may be compiled from various sources to monitor interactions within a healthcare environment. Both interactions with individuals and interactions with a healthcare system may be monitored. Location data, clinical data, and system data, among others, may be combined to monitor the healthcare environment. By combining the data from various sources, a user is able to get a complete picture of the healthcare environment to, for example, optimize workflows, analyze changes made to a healthcare environment and the impacts thereof, provide a true ROI in change by measuring baselines before and after a change is introduced, and the like.

Having briefly described embodiments of the present invention, an exemplary operating environment suitable for use in implementing embodiments of the present invention is described below. Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer-readable media, for instance, database cluster 104. Computer-readable media can be any available media that may be accessed by server 102, and includes volatile and nonvolatile media, as well as removable and non-removable media. By way of example, and not limitation, computer-readable media may include computer storage media and communication media. Computer storage media may include, without limitation, volatile and non-volatile media, as well as removable and nonremovable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 104, provide storage of computer-readable instructions, data structures, program modules, and other data for the server 102.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home healthcare environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 108 may also be physically located in nontraditional medical care environments so that the entire healthcare community may be capable of integration on the network. The remote computers 108 may be personal computers, servers, routers, network PCs, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are not further disclosed herein.

Figure 2:
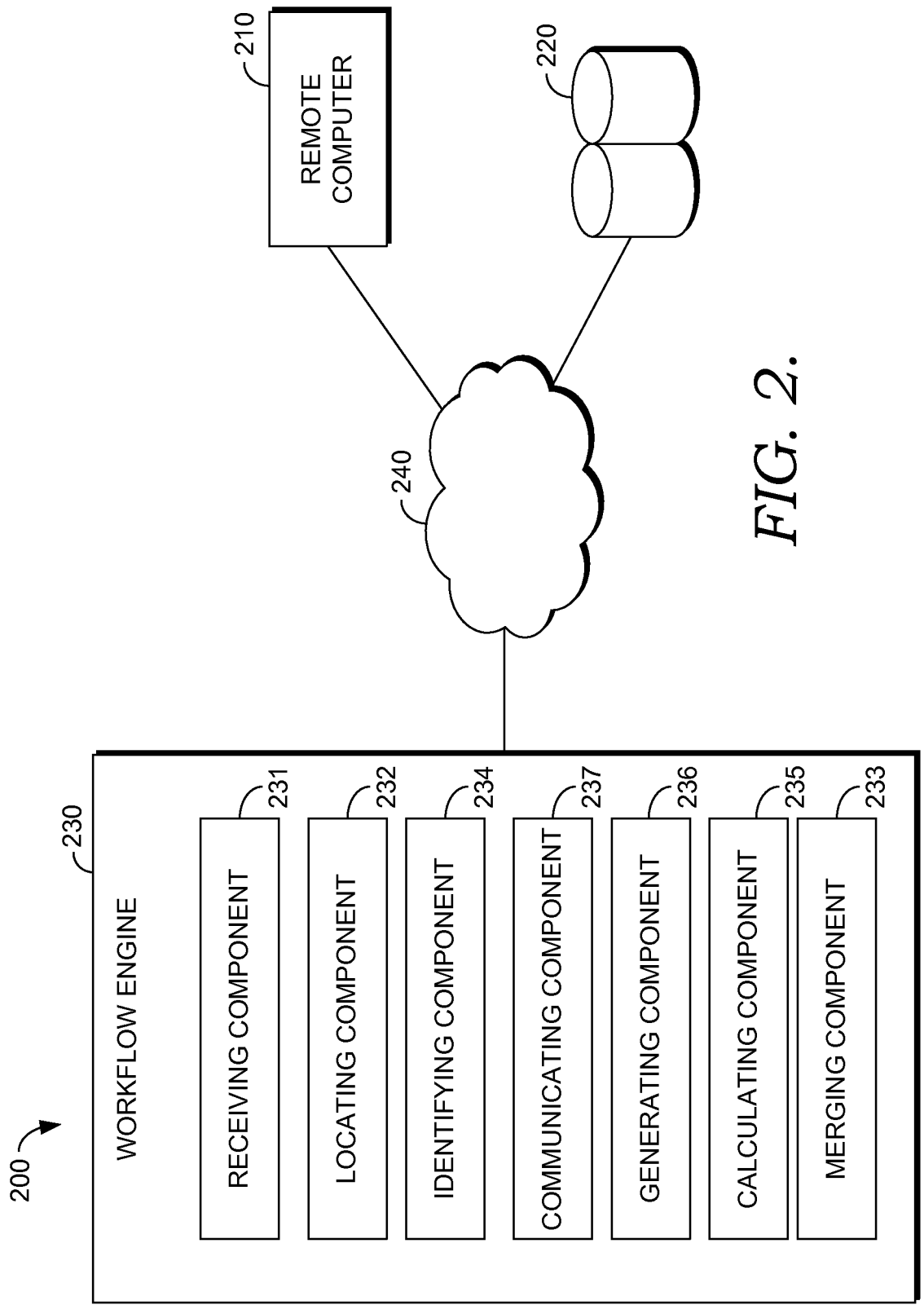
FIG. 2 is an exemplary system architecture suitable to implement embodiments of the present invention.

Turning to FIG. 2, an architectural framework 200 is shown for monitoring a healthcare environment. This architectural framework 200 may operate, for instance, within the context of the exemplary medical information system 100 of FIG. 1. The system of FIG. 2 includes a remote computer 210, a database 220, a workflow engine 230, and a network 240. Other components not shown here may also be used to carry out aspects of the present invention. Further, several components shown in FIG. 2 may be combined into a single component although shown separately in FIG. 2. Alternatively, components, such as the database 220, although shown as a single component, may actually be two or more components.

The workflow engine 230 includes a receiving component 231, a locating component 232, a merging component 233, an identifying component 234, a calculating component 235, a generating component 236, and a communicating component 237. Each component of the workflow engine 230 may assist in receiving, identifying, storing, communicating, or the like, information to monitor healthcare environments. The workflow engine 230 may be associated with a healthcare entity. Healthcare entities may include, but are not limited to, clinicians, hospitals, clinics, pharmacies, laboratories, and the like. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like.

Healthcare environments are constantly seeking to increase efficiency, to improve productivity, to improve quality of care, among other things. Sometimes these things are accomplished by making changes to procedures, workflows, or the like. Significant changes, however, do not come without a cost, either monetary or otherwise. Healthcare environments, like any other entity, are conscious of their ROI. A ROI, as used herein, refers generally to a ratio of money gained or lost on an investment relative to an amount of money invested. ROI is critical is making decisions and a true ROI makes the decision much easier for a decision-maker.

To provide a true ROI and to monitor a healthcare environment and the changes therein, data from various sources may be combined to provide a complete picture of the healthcare environment. Exemplary data to combine may be clinical data, location data, and system data, among other things. Clinical data, as used herein, refers generally to data that is associated with a healthcare environment. Clinical data may include, but is not limited to, patient documents, patient data, clinician information, facility data, clinical notes, summaries, reports, analyses, orders, or other types of electronic medical documentation relevant to a particular patient's condition and/or treatment. Clinical data may also include information regarding equipment of a healthcare environment. For instance, an order that requires a specific piece of equipment in order to complete the order may be identified as requiring the specific piece of equipment. Additionally, maintenance information for all equipment may be included in the clinical data.

Location data, as used herein, refers generally to a location of a clinician, a patient, a piece of equipment, or the like. The location may be within the healthcare environment. Location data may be obtained by way of identifiers (e.g., patient identifiers, clinician identifiers, equipment identifiers, etc.). The identifiers may be tracked via a plurality of sensors located in the healthcare environment. The sensors may utilize a real-time location services technology such as ultrasound technology, infrared technology, radio-frequency identification (RFID) technology, or the like. Using said technology, the sensors send out signals to identifiers. The signals are received by the identifiers and the identifiers respond to the signals. A response from an identifier is received by the sensors and the sensors are able to recognize and determine the location of the responding identifier.

System data, as used herein, refers generally to data that is associated with a user action within the healthcare environment. In other words, the system data adds the "action" to the location of a clinician such that the location data identifies where a clinician is at a given point in time and the system data identifies what the clinician is doing. For example, assume that a nurse is retrieving a medication from a medication dispensing unit. An exemplary medication dispensing unit is RxStation® by Cerner Corporation. The nurse will be required to enter an access code to gain access to the medication dispensing unit. The access code is an interaction with the healthcare environment and is identified as system data. Thus, a location of the nurse indicates that the nurse is near the medication dispensing unit and the access code (i.e., system data) indicates that the nurse is obtaining a medication.

Going one step further, clinical data may indicate why the nurse is obtaining the medication. For example, a patient assigned to the nurse may have an outstanding order for administration of the medication obtained by the nurse. Thus, a combination of the location data, the system data, and the clinical data tell us where the nurse is, what the nurse is doing, and why the nurse is doing the action.

System data may also be a combination of user selections. For instance, a particular sequence of user selections or "clicks," for example, within a documentation program may indicate that a user is documenting administration of a medication, vital signs, or the like. Thus, a plurality of user selections may be identified as representing one or more clinical events. Clinical events include, but are not limited to, non-invasive procedures, surgical procedures, tests, evaluations, examinations, consultations, documentations, or the like.

Returning to FIG. 2, the receiving component 231 is configured to receive requests input into the remote computer 210 by a user. The user may be a clinician or a non-clinician and the request may be a request to generate a view of a healthcare environment, as will be discussed in detail below. The receiving component 231 is also configured to receive location data, clinical data, and system data. The clinical data, system data, and location data may be received from the database 220. The location data may also be received from the locating component 232.

Figure 3:
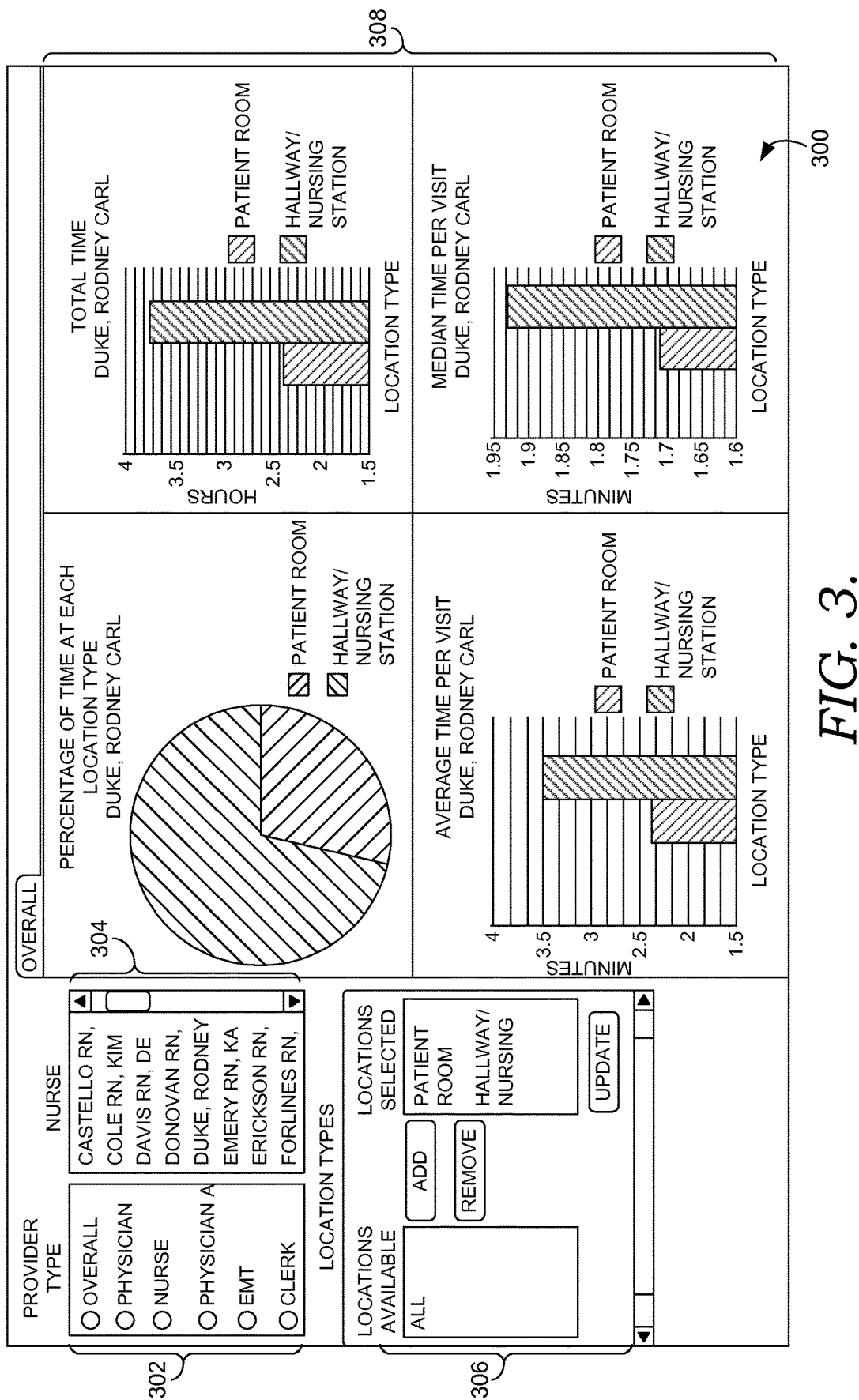
FIG. 3 is a screenshot illustrating an exemplary dashboard interface, in accordance with embodiments of the present invention.

The request may be a request to generate a view of a healthcare environment. The view of the healthcare environment may be provider-specific, location-specific, a combination thereof, of the like. An exemplary dashboard 300, which may provide a view of the healthcare environment, is provided in FIG. 3. The dashboard includes a provider-type area 302, a provider selection area 304, a location selection area 306, and a display area 308. The provider-type area 302 is configured to receive a selection of a type of provider in a healthcare environment. The type of provider may be a physician, nurse, nurse practitioner, physician assistant, radiology technician, clerk, or the like. As illustrated in the exemplary dashboard 300, a nurse has been selected in the provider-type area 302.

Upon selecting a provider-type, a user can then select a specific provider from the provider selection area 304. The provider selection area 304 may include all providers of a healthcare environment. The provider selection area 304 may also be narrowed down to only display providers associated with the selected provider-type. For instance, in the provider-type area 302, a nurse has been selected so the provider selection area 304 has been filtered to only indicate providers that are associated with the provider-type "nurse." The dashboard 300 may also provide a patient selection area (not shown) such that a user may narrow the view by patient information as well.

The location selection area 306 is configured to receive a selection of one or more locations with the healthcare environment. As illustrated in the dashboard 300, the user has selected a patient room and a hallway/nursing station to narrow the view. The patient room may be a specific patient's room or may be any/all patients' rooms. Similarly, the hallway/nursing station may be a particular hallway or nursing station or any/all hallways or nursing stations.

Once the criteria are selected by the user, the display area 308 displays data associated with the selected criteria. The display area 308 in the illustrated dashboard 300 provides a view of time spent at a specified location. For example, the display 308 indicates a percentage of time at each selected location by the selected provider, an average time per visit, a total time, and a median time per visit. The display area 308 of the dashboard 300 may be configured to display any data desired by a user.

Returning to FIG. 2, upon receiving the request, the receiving component 231 receives location data, clinical data, and system data necessary to complete the request. All or some of the data may be received from the database 220. In an embodiment, the locating component 232 is separate from the database 220. Once the data is received, the merging component 233 merges the location data, the clinical data, and the system data together. By merging the data together, it is possible for a user to view not only where a clinician is located, but also what the clinician is doing and why the clinician is doing the same.

Once the data is merged, the identifying component 234 identifies clinical events from the system data. For example, one or more user selections may be associated with a specific clinical event such as a sequence of user selections into a software system being associated with a clinician documenting vital signs of a patient.

Additionally, once the data is merged, the calculating component 235 may calculate one or more requested calculations. The requested calculations may be an amount of time spent in a location, an amount of time spent with a patient, an amount of time spent completing a task, a comparison of an amount of time currently required versus an amount of time previously required (before a change in procedure, for example), and the like. By way of example only, assume that a healthcare environment has decided to relocate a resource (e.g., a piece of equipment such as a portable ultrasound machine). The calculating component 235 may calculate a time required to acquire the resource and compare that time to a time that was previously required to acquire the resource before the resource was relocated. Calculations based on objective evidence provide a true ROI as the user is able to see the amount of time saved as well as other data influenced by a change. The objective evidence also provides reliable indicators of changes that improve workflows or may improve workflows.

Figure 4:
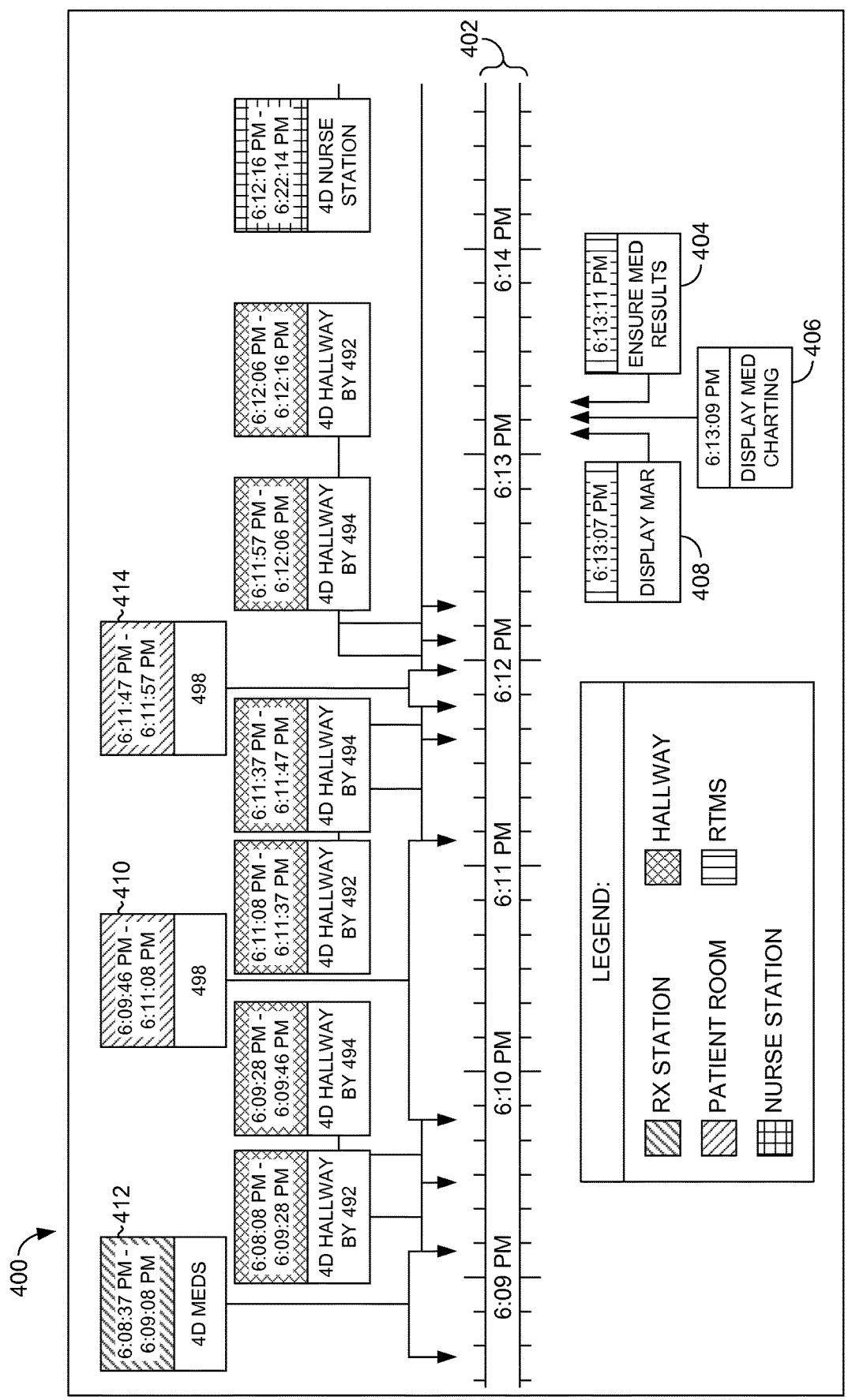
FIG. 4 is a screenshot illustrating an exemplary timeline interface, in accordance with an embodiment of the present invention.

Once the calculations are complete, the generating component 236 may create a view of the healthcare environment. The view of the healthcare environment may be generated as a dashboard, as previously provided as the dashboard 300 of FIG. 3. The view of the healthcare environment may also be generated as a timeline 400, as provided in FIG. 4. The timeline 400 includes a timeline display area 402 and one or more user detections 404-414. The user detections 404-414 may be location data, system data, clinical data, or the like. For instance, the user detections 410 and 414 are location data indicating the clinician is in a patient room indicated as patient room 498 in FIG. 4.

In an embodiment, the timeline 400 is useful in monitoring compliance procedures of a healthcare environment. For instance, assuming that a healthcare environment requires documentation of administration of a medication to a patient while inside the patient's room, a timeline, such as the timeline 400 of FIG. 4, may be used to monitor compliance with this procedure. By way of example only, user detection 412 indicates that the clinician has obtained a medication. The timeline 400 also indicates that the user entered patient room 498 at a specified time. However, the system data, indicated in user detections 406-408, indicates that the medication was not entered in the patient's chart until after the clinician left the patient's room (as evidenced by the time stamp and the location information for the clinician). As indicated in the timeline 400, the clinician was located in the hallway during user detections 404-408. Thus, assuming the healthcare environment required documentation within a patient's room, the timeline 400 would be useful to identify a non-compliant clinician, among other things.

Such identification of violations of compliance procedures may be communicated to the user by any means known in the art. For example, a pop-up notification may be displayed, an electronic mail message may be communicated, a message on a mobile device may be communicated, or the like.

Returning to FIG. 2, upon generating the view of the healthcare environment, the view is communicated to the remote computer 210 by the communicating component 237. Additionally, any necessary notifications, as described above with reference to FIG. 4, may also be communicated by the communicating component 237 to the remote computer 210 or any authorized user.

While the above-described system 200 has been detailed with respect to receiving a request for a view of a healthcare environment, the system 200 may also automatically monitor the healthcare environment without any user intervention. For instance, the system 200 may constantly update a view of a healthcare environment such that regulatory compliance issues, for example, are always monitored.

Additionally, the system 200 has the ability to not only monitor the healthcare environment, but to also suggest workflow changes to result in increased compliance, increased efficiency, patient satisfaction, and the like. For instance, upon detecting that a clinician spends a large amount of time searching for/gathering resources (e.g., supplies, equipment, etc.), the system 200 may suggest that the resources be relocated, that a new resource station should be added to the healthcare environment, or the like. The system 200 may include predefined criteria to monitor. The predefined criteria may be specified by the user.

Figure 5:
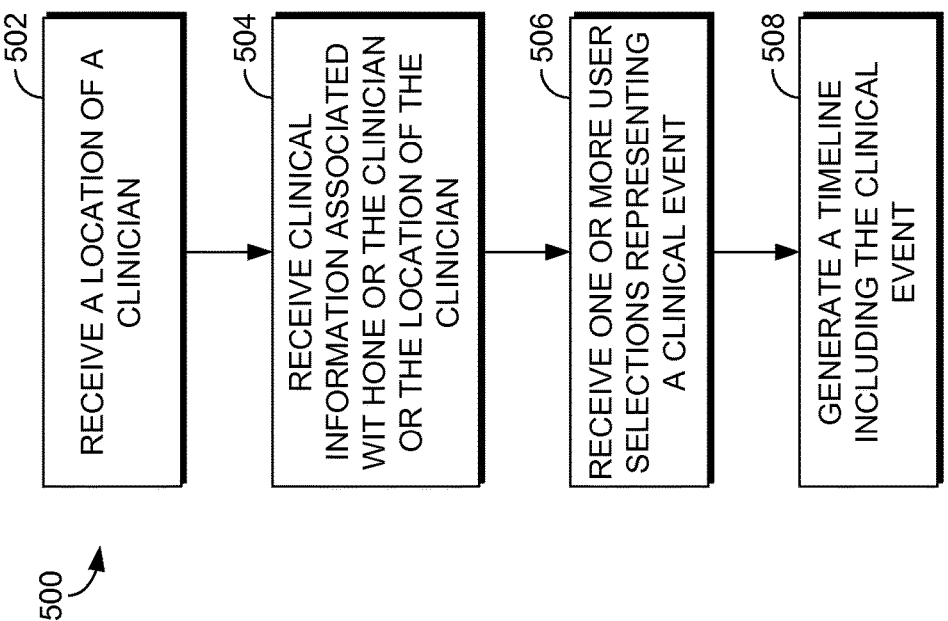
FIG. 5 is a flow diagram illustrating a first exemplary method for optimizing workflows, in accordance with an embodiment of the present invention.

Turning now to FIG. 5, a flow diagram showing a method 500, in accordance with an embodiment of the present invention, is provided. Initially, at block 502 a location of a clinician is received. At block 504, clinical information associated with one of the clinician or the location of the clinician is received. At block 506, one or more user selections representing a clinical event is received. At block 508, a timeline including the clinical event is generated.

Figure 6:
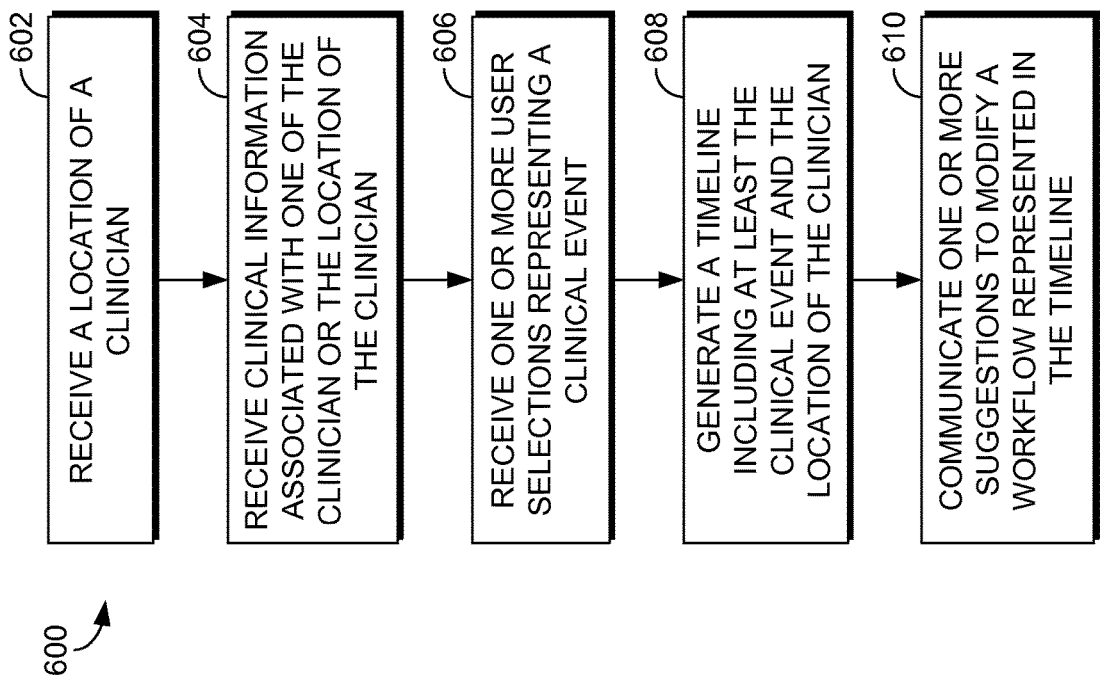
FIG. 6 is a flow diagram illustrating a second exemplary method for optimizing workflows, in accordance with an embodiment of the present invention.

Referring to FIG. 6, a flow diagram showing a method 600, in accordance with an embodiment of the present invention, is provided. Initially, at block 602, a location of a clinician is received. At block 604, clinical information associated with one of the clinician or the location of the clinician is received. At block 606, one or more user selections representing a clinical event are received. At block 608, one or more suggestions to modify a workflow represented in a view of the healthcare environment are communicated.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more non-transitory computer storage media storing computer-useable instructions that, when used by one or more computing devices in a computer system associated with a healthcare environment, cause the one or more computing devices to perform a method comprising:
   receiving a request via a computer network from a remote computing device to provide a timeline view of the healthcare environment based on a time of one or more user detections;
   determining location information of a clinician utilizing a clinician identifier that is tracked within the healthcare environment, wherein the clinician identifier is tracked via a plurality of sensors distributed in the healthcare environment utilizing a real-time location services technology, wherein the location information includes a location of the clinician;
   receiving clinical information associated with a resource required to complete a task;
   receiving one or more clinician interactions within the computer system including one or more user selections by the clinician that is associated with a clinical event;
   determining the clinical event from system data by detecting and monitoring the system data within the computer system associated with the one or more clinician interactions, wherein the one or more clinician interactions include entries and selections into one or more software programs that reside on a memory associated with the computer system;
   merging the location information, the clinician information and the system data into a merged data;
   determining the one or more user detections including at least one of the clinical event, the clinical information, and the location of the clinician;
   determining the time of each of the one or more user detections from the system data, the clinical information, and the location information;
   utilizing the clinical event, the clinical information, and the location of the clinician, generating and displaying a timeline on a timeline interface at the remote computing device via the computer network, wherein the timeline interface includes a timeline display area and the one or more user detections displayed on the timeline at one or more positions based on the time of each of the one or more user detections;
   determining a time to complete a task from the merged data;
   and
   based upon a comparison between one or more healthcare environment requirements, the time to complete the task, and the timeline, determining and displaying a recommendation for at least one procedural alteration to increase regulatory compliance on the remote computing device, wherein the at least one procedural alteration includes relocating the resource required to complete the task upon identifying that the clinician spent an amount of time exceeding a predetermined threshold searching for the resource.

2. The media of claim 1, wherein the real-time location services technology is one of ultrasound technology, infrared technology, or radio-frequency identification technology.

3. The media of claim 1, wherein the received clinical information comprises a healthcare order that has been input by the clinician.

4. The media of claim 1, wherein the clinical event is a task that has been completed by the clinician for a patient.

5. The media of claim 1, wherein the method further comprises:
   associating the clinical event with a current location of the clinician; and
   identifying whether completion of the clinical event violates compliance procedures.

6. The media of claim 5, wherein the method further comprises communicating a notification of conformity with or violation of the compliance procedures.

7. One or more non-transitory computer storage media storing computer-useable instructions that, when used by one or more computing devices in a computer system associated with a healthcare environment, cause the one or more computing devices to perform a method comprising:
   determining location information of a clinician utilizing a clinician identifier that is tracked within a healthcare environment, wherein the clinician identifier is tracked via a plurality of sensors distributed in the healthcare environment utilizing a real-time location services technology;
   receiving clinical information associated with a resource required to compete a task;

receiving one or more clinician interactions within the computer system including one or more user selections by the clinician that is associated with a clinical event;

determining the clinical event from system data by detecting and monitoring the system data within the computer system associated with the one or more clinician interactions, wherein the one or more clinician interactions include entries and selections into one or more software programs that reside on a memory associated with the computer system;

merging the location information, the clinician information and the system data into a merged data;

determining a time to complete a task from the merged data; and based on a comparison between one or more healthcare environment requirements and one or more of the clinical event, the clinical information, a location of the clinician, and the time to complete the task, determining and communicating via a remote computing device one or more recommendations to modify at least one procedural component of a workflow represented in a view of the healthcare environment to increase regulatory compliance, wherein the one or more suggestions to modify the at least one procedural component of the workflow includes relocating the resource required to complete the task upon identifying that the clinician spent an amount of time exceeding a predetermined threshold searching for the resource.

8. The media of claim 7, wherein the method further comprises:

determining whether healthcare compliance procedures have been violated;

based upon a determination that the healthcare compliance procedures have been violated, communicating a notification of a violation to a user.

9. The media of claim 7, wherein the real-time location services technology is one of ultrasound technology, infrared technology, or radio-frequency identification technology.

10. The media of claim 1, wherein the location of the clinician is associated with a time stamp.

11. The media of claim 1, wherein the method further comprises generating a view of the healthcare environment based on the timeline.

12. The media of claim 11, wherein the method further comprises communicating the view of the healthcare environment to a user.

13. The media of claim 7, wherein the clinical database includes one or more patient's electronic health records.

14. The media of claim 7, wherein the method further comprises utilizing the clinical event, the clinical information, and the location of the clinician, generating a timeline including the clinical event.

15. The media of claim 7, wherein the received clinical information comprises a healthcare order that has been input by the clinician.

16. The media of claim 7, wherein the clinical event is a task that has been completed by the clinician for a patient.

17. The media of claim 7, wherein the location of the clinician is associated with a time stamp.

18. The media of claim 7, wherein the method further comprises generating a view of the healthcare environment based on the timeline.

19. The media of claim 18, wherein the method further comprises communicating the view of the healthcare environment to a user.

* * * * *

UNITED STATES PATENT AND TRADEMARK OFFICE
CERTIFICATE OF CORRECTION

PATENT NO. : 11,392,872 B2
APPLICATION NO. : 14/585306
DATED : July 19, 2022
INVENTOR(S) : David Compton et al.

It is certified that error appears in the above-identified patent and that said Letters Patent is hereby corrected as shown below:

On the Title Page

Item (71), Applicant, Line 1, delete "CERNER INNOVATIONS, INC.," and insert -- CERNER INNOVATION, INC., --.

Item (74), Attorney, Agent, or Firm, Line 1, delete "Shook Hardy & Bacon," and insert -- Shook, Hardy & Bacon, --.

Under OTHER PUBLICATIONS, Line 10, delete "US." and insert -- U.S. --.

In the Drawings

Sheet 5 of 5, Fig. 5, Reference Numeral 504, delete "WIT HONE" and insert -- WITH ONE --.

In the Specification

Column 3, Line 54, delete "Electronic" and insert -- Electronics --.

Signed and Sealed this
Twenty-fourth Day of January, 2023

Katherine Kelly Vidal
*Director of the United States Patent and Trademark Office*